(12) United States Patent
Trexler et al.

(10) Patent No.: US 12,295,826 B2
(45) Date of Patent: *May 13, 2025

(54) REPAIR PROSTHETIC CURL MITIGATION

(71) Applicant: C.R. Bard, Inc., Murray Hill, NJ (US)

(72) Inventors: Jonathan Bruce Trexler, Rehoboth, MA (US); Augustus Felix, Cranston, RI (US); Tami L. Rathbun, Exeter, RI (US); Cameron Michael Correia, Warwick, RI (US); Tyler William Marshall, Andover, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/604,732

(22) Filed: Mar. 14, 2024

(65) Prior Publication Data

US 2024/0216119 A1 Jul. 4, 2024

Related U.S. Application Data

(63) Continuation of application No. 18/186,240, filed on Mar. 20, 2023, now Pat. No. 11,957,559, which is a (Continued)

(51) Int. Cl.
*A61F 2/00* (2006.01)
*A61B 17/06* (2006.01)

(52) U.S. Cl.
CPC ...... *A61F 2/0063* (2013.01); *A61B 17/06166* (2013.01); *A61F 2002/0072* (2013.01); (Continued)

(58) Field of Classification Search
CPC ....... A61B 17/06166; A61F 2002/0072; A61F 2220/0008; A61F 2220/0075; (Continued)

(56) References Cited

U.S. PATENT DOCUMENTS 5,141,515 A  8/1992 Eberbach
5,397,331 A  3/1995 Himpens et al.
(Continued)

FOREIGN PATENT DOCUMENTS

CN  103476364 A  12/2013
CN  104510544 A  4/2015
(Continued)

OTHER PUBLICATIONS

International Search Report and Written Opinion dated Jan. 31, 2019, in connection with International Application No. PCT/US2018/051460.

*Primary Examiner* — Darwin P Erezo
*Assistant Examiner* — Brigid K Byrd
(74) *Attorney, Agent, or Firm* — Wolf, Greenfield & Sacks, P.C.

(57) ABSTRACT

A repair prosthetic for repairing a hernia is disclosed. In some embodiments, the repair prosthetic includes a patch body, a frame that assists in spreading the patch body from a reduced configuration to an expanded configuration, and a plurality of tethers attached to the patch body at locations between the frame and a periphery of the patch body. In various embodiments, the tethers can be tensioned to mitigate curling or creasing in the patch body to flatten the patch to facilitate attachment to tissue.

18 Claims, 7 Drawing Sheets

Related U.S. Application Data continuation of application No. 16/829,631, filed on Mar. 25, 2020, now Pat. No. 11,633,271, which is a continuation of application No. 15/782,120, filed on Oct. 12, 2017, now Pat. No. 10,624,729.

(52) U.S. Cl.
CPC ............... *A61F 2220/0008* (2013.01); *A61F 2220/0075* (2013.01); *A61F 2230/0004* (2013.01); *A61F 2230/0058* (2013.01)

(58) Field of Classification Search
CPC ...... A61F 2230/0004; A61F 2230/0058; A61F 2/0063
See application file for complete search history.

(56) References Cited

U.S. PATENT DOCUMENTS

| | | | |
|---|---|---|---|
| 5,405,360 | A | 4/1995 | Tovey |
| 6,391,060 | B1* | 5/2002 | Ory ..................... A61F 2/0063 606/151 |
| 6,575,988 | B2 | 6/2003 | Rousseau |
| 6,669,735 | B1 | 12/2003 | Pelissier |
| 6,790,213 | B2 | 9/2004 | Cherok et al. |
| 6,911,037 | B2 | 6/2005 | Gainor et al. |
| 9,649,331 | B2 | 5/2017 | Eaton et al. |
| 10,624,729 | B2 | 4/2020 | Rathbun et al. |
| 11,633,271 | B2 | 4/2023 | Trexler et al. |
| 11,957,559 | B2 | 4/2024 | Trexler et al. |
| 2002/0103494 | A1 | 8/2002 | Pacey |
| 2006/0189918 | A1* | 8/2006 | Barker ............... A61B 17/0057 604/15 |
| 2007/0185506 | A1 | 8/2007 | Jackson |
| 2007/0299043 | A1 | 12/2007 | Hunter et al. |
| 2008/0069857 | A1 | 3/2008 | Yeo et al. |
| 2008/0147200 | A1 | 6/2008 | Rousseau et al. |
| 2009/0082792 | A1 | 3/2009 | Koyfman et al. |
| 2009/0254103 | A1 | 10/2009 | Deutsch |
| 2010/0069930 | A1 | 3/2010 | Roslin et al. |
| 2011/0295283 | A1 | 12/2011 | Darois et al. |
| 2012/0209301 | A1* | 8/2012 | Bell .................... A61B 17/0485 606/151 |
| 2013/0060263 | A1* | 3/2013 | Bailly ................. A61F 2/0063 606/151 |
| 2014/0194926 | A1* | 7/2014 | Bailly ................. A61F 2/0063 606/213 |
| 2015/0157436 | A1 | 6/2015 | Bailly et al. |
| 2015/0157437 | A1* | 6/2015 | Cohen ................. A61B 17/06 606/151 |
| 2015/0305847 | A1 | 10/2015 | Roll et al. |
| 2016/0151136 | A1 | 6/2016 | Hamilton et al. |
| 2017/0181831 | A1 | 6/2017 | Felix et al. |
| 2019/0110878 | A1 | 4/2019 | Rathbun et al. |
| 2023/0225848 | A1 | 7/2023 | Trexler et al. |

FOREIGN PATENT DOCUMENTS

| | | |
|---|---|---|
| DE | 698 01 447 T2 | 12/2001 |
| WO | WO 2007/115110 A2 | 10/2007 |
| WO | WO 2010/059234 A1 | 5/2010 |

* cited by examiner

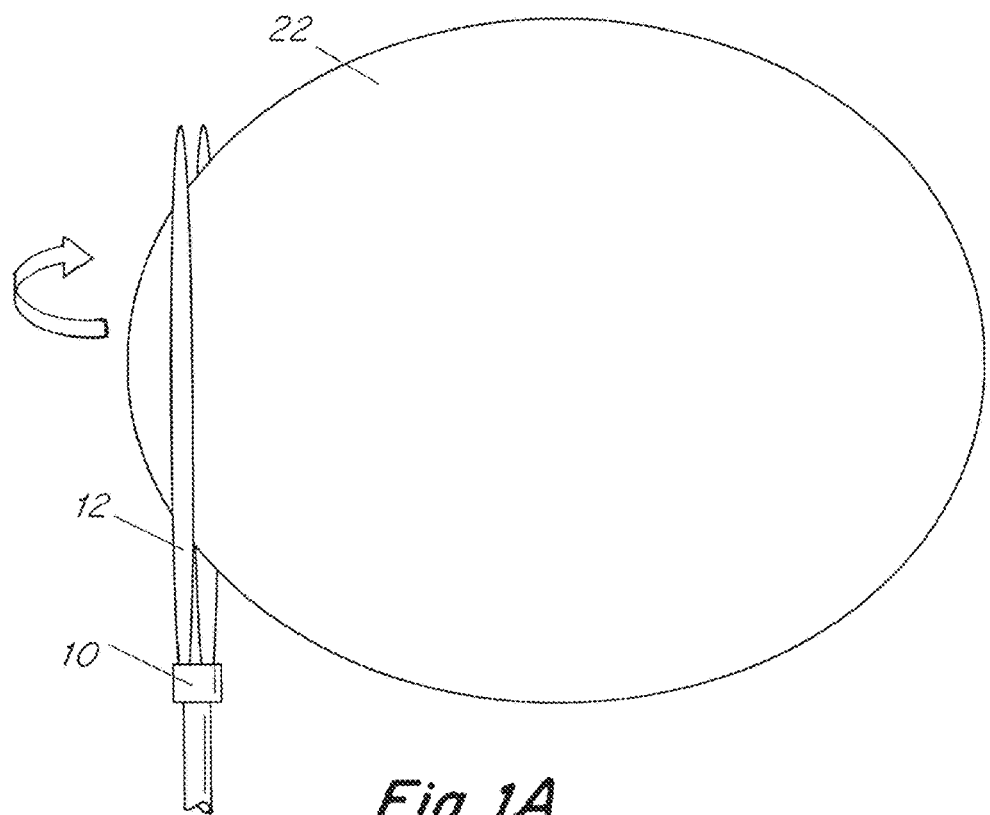
Fig. 1A
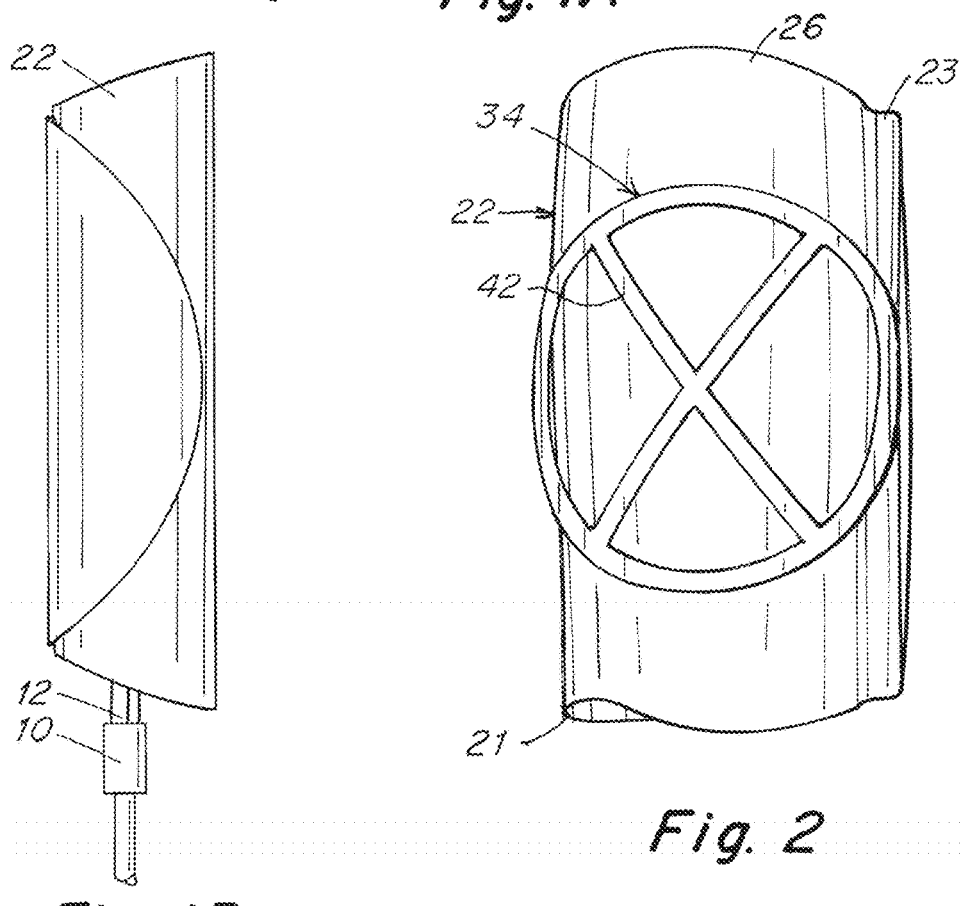
Fig. 1B
Fig. 2

REPAIR PROSTHETIC CURL MITIGATION

RELATED APPLICATIONS

This application is a continuation of U.S. application Ser. No. 18/186,240, filed Mar. 20, 2023, which is a continuation of U.S. application Ser. No. 16/829,631, filed on Mar. 25, 2020, which is a continuation of U.S. application Ser. No. 15/782,120, filed on Oct. 12, 2017, the contents of which are herein incorporated by reference in their entirety.

FIELD

Embodiments related to repair prosthetic curl mitigation are disclosed.

BACKGROUND

A hernia defect is an opening or weakness in a tissue or muscle wall, such as the abdominal wall. One approach for repairing a hernia is to cover the tissue or muscle wall defect with a patch of repair fabric or mesh. The patch may be placed in an open procedure or through a minimally invasive procedure, such as by a laparoscopic technique.

In a laparoscopic hernia repair, a patch may be rolled up and delivered through a narrow cannula to a treatment site. After laparoscopic deployment, a resilient support member, such as a resilient frame, associated with the patch may expand the patch to an enlarged deployed configuration. The expanded patch including the resilient support member is then fixated to the tissue or muscle wall over the defect using sutures, staples, tacks and/or other fixation elements. For example, such fixation elements may be applied around a border region, and/or at other locations, of the patch into healthy tissue surrounding the defect. In some instances a repair prosthetic may include a central tether attached to the frame in such a manner that a free end of the central tether may be drawn through the abdominal wall to outside of the patient. Continued pulling of the central tether biases the frame, and the associated patch body of the repair prosthetic upwardly against the abdominal wall. Biasing the repair prosthetic against the abdominal wall helps to facilitate holding the repair prosthetic in place during fixation.

SUMMARY

In one embodiment, a repair prosthetic for repairing a hernia defect may include a patch body with a periphery and a frame attached to the patch body. The frame assists in spreading the patch body from a reduced configuration to an expanded configuration. The repair prosthetic also includes a primary tether extending away from the patch body and a plurality of tethers attached to the primary tether, and where each tether extends from the primary tether to an attachment location with the patch body located radially outward from the frame. Pulling the primary tether in a direction away from the patch body tensions the plurality of tethers.

In another embodiment, a repair prosthetic for repairing a hernia defect includes a patch body having a periphery, a frame attached to the patch body that assists in spreading the patch body from a reduced configuration to an expanded configuration, and a plurality of tethers. The plurality of tethers are attached to the patch body at locations between or at the frame and the periphery of the patch body. At least two of the plurality of tethers are located on opposing sides of the patch body.

In yet another embodiment a prosthetic for repairing a hernia defect is applied as follows. The prosthetic is delivered in a reduced configuration through an opening into a patient, where the prosthetic includes a patch body with a periphery. The patch body is then spread to an expanded configuration about the hernia defect with a frame attached to the patch body. A primary tether is then pulled in a direction away from the patch body to tension a plurality of tethers attached to the patch body at locations between the frame and the periphery of the patch body.

In still another embodiment, a prosthetic for repairing a hernia defect is applied as follows. The prosthetic is delivered in a reduced configuration through an opening into a patient, where the prosthetic includes a patch body with a periphery. The patch body is then spread to an expanded configuration about the hernia defect with a frame attached to the patch body. A plurality of tethers, attached to the patch body at locations between or at the frame and the periphery of the patch body, are then pulled. At least two of the plurality of tethers are located on opposing sides of the patch body.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 1A shows a top view of a repair prosthetic and introducer in the process of rolling up the repair prosthetic for insertion in a reduced configuration;

FIG. 1B shows a top view of the repair prosthetic and introducer in the rolled up configuration;

FIG. 2 shows a perspective view of the repair prosthetic after being rolled up and expanded to an expanded configuration;

Figure 3A:
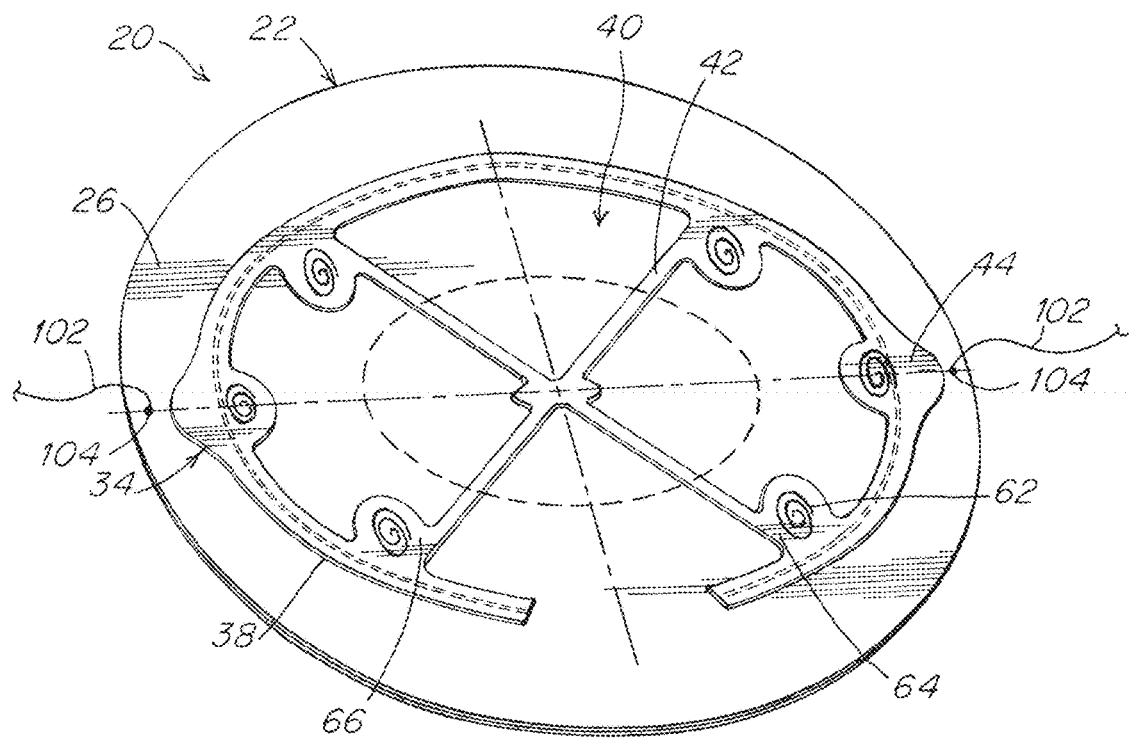
FIG. 3A shows a top perspective view of a repair prosthetic including a curl mitigation system according to one embodiment.

It should be understood that aspects of the invention are described herein with reference to certain illustrative embodiments and the figures. The illustrative embodiments described herein are not necessarily intended to show all aspects of the invention, but rather are used to describe a few illustrative embodiments. Thus, aspects of the invention are not intended to be construed narrowly in view of the illustrative embodiments. In addition, it should be understood that aspects of the invention may be used alone or in any suitable combination with other aspects of the invention.

DETAILED DESCRIPTION

In a minimally invasive surgical technique, as well as in certain open procedures, a repair prosthetic including a repair patch with a patch body may be reduced in size to facilitate delivery of the repair prosthetic to the treatment site. For example, in a laparoscopic procedure, the repair prosthetic may be rolled into a cylindrical shape, or otherwise collapsed into a smaller reduced configuration, suitable for passage through a cannula to the surgical site. However, a repair prosthetic may exhibit curls, creases, and/or other surface irregularities of the patch body after being expanded to an expanded configuration. The amount of curls, creases, and/or other surface irregularities may be due to a number of variables including, but not limited to, materials, thicknesses, sizes, and shape of the repair patch and associated frame as well as a diameter the repair prosthetic is reduced to during delivery to a surgical site. In either case, the Inventors have recognized that reducing the amount of curl, i.e. flattening, the repair prosthetic after deployment may help ensure proper contact between the repair prosthetic and adjacent tissue.

In view of the above, the Inventors have contemplated that it may be desirable to reduce, or eliminate, curling and/or other surface irregularities of a patch body of a repair prosthetic when it is expanded from a reduced configuration to an expanded configuration by an associated frame. Specifically, the Inventors have recognized the benefits associated with a repair prosthetic including a plurality of tethers connected with different portions of a patch body of the repair prosthetic between an associated frame of the repair prosthetic and an outer periphery of the patch body. As elaborated on below in regards to specific embodiments, tensioning of these tethers may aid a surgeon in mitigating, or eliminating, the presence of curl and other surface irregularities of a patch body of a repair prosthetic. In some embodiments, these tethers may also be used to help aid in positioning the repair prosthetic during use. Thus, the patch body of a repair prosthetic may be held relatively taut and/or flat against a tissue surface which may facilitate fixating the repair prosthetic to the tissue.

In one embodiment a repair prosthetic includes a patch body and a frame attached to the patch body. The frame assists in expanding the patch body from a reduced configuration, e.g. a rolled up configuration, to an expanded configuration in which the repair prosthetic is attached to tissue after delivery to a surgical site. The repair prosthetic may include at least two tethers that are connected to different portions of the patch body. In some embodiments the at least two tethers are attached to diametrically opposing portions of the patch body located on either side of a central of the patch body. The tethers may also be attached to the patch body at a location that is between the frame and an outer periphery of the patch body. Accordingly, when the patch body has been positioned against a tissue surface including a defect, such as a hernia located in an abdominal wall, a user may tension the two or more tethers to mitigate any curling or creasing of the patch body before affixing the repair prosthetic to the tissue.

While only two tethers are mentioned above, any number of tethers may be used. Additionally, the various tethers may include pairs of tethers that are located diametrically opposite from one another on opposing portions of the patch body. Alternatively, a plurality of tethers may simply be spaced around either portions or the entire periphery of the patch body. Accordingly, it should be understood that any number of tethers may be used and they may be attached at any desired location along a periphery of a patch body as the disclosure is not so limited.

In some embodiments, it may be desirable to have a single primary tether that may be manipulated to mitigate curling of a repair prosthetic instead of manipulating multiple individual tethers either sequentially or at the same time during deployment of the repair prosthetic. Similar to the above, in some embodiments, a repair prosthetic may include at least two tethers attached to opposing portions of a patch body of the repair prosthetic at locations that are between a periphery of the patch body and an associated frame attached to the patch body. The tethers extend in a direction directed inwards from a periphery of the patch body towards an interior portion, and in some embodiments a center, of the patch body. Either the ends of the individual tethers, or a single primary tether the individual tethers are attached to, may extend through an aperture formed in either the frame and/or patch body. Accordingly, either the individual tethers, or primary tether may be pulled through the aperture to tension the at least two tethers, which due to the presence of the frame apply a force and/or moment to bias the patch body to an uncurled, or flat, configuration.

In the above embodiment it may be desirable to have a tether arrangement that allows a user to selectively adjust the amount of tension applied to the various tethers of a repair prosthetic, and thus, the anti-curling force applied to different portions of a patch body of the repair prosthetic. In one such embodiment the tethers extend from the periphery of the patch body toward and through an aperture through a frame and/or patch body of the repair prosthetic. The tethers may include stops on either side of the aperture to permit the tension of each tether to be adjusted within a range dictated by a location of the stops along a length of the tethers. In some embodiments, two tethers may be formed by a single length of material including two separate pairs of associated stops. In such an embodiment, a tether including a first pair of stops located on either side of an aperture may form a loop that extends back through the aperture with a second pair of stops located on either side of the aperture. That portion of the tether is then attached to an opposing portion of the patch body. Due to the presence of the two pairs of stops, the tensioning and/or displacement of the two tethers may be adjusted individually within the ranges dictated by the stops.

In some embodiments it may be desirable to hold a repair prosthetic against a tissue surface it is to be affixed to. In one such embodiment, a repair prosthetic may include a primary, or central, tether that is connected to the frame and/or patch body of a repair prosthetic. In use, a user may capture and pull the primary tether through tissue of the patient using a suture passer or other appropriate device to hold the repair prosthetic against the tissue surface, e.g. against an abdominal wall. In some embodiments, the primary tether may be formed from the plurality of other individual tethers. In either case, in the above noted embodiment, the primary tether, and/or the ends of the individual tethers attached to the repair patch body may be used to hold a repair prosthetic against tissue and apply tension to the individual tethers at the same time. Such a configuration may beneficially permit a surgeon to adjust the amount of tensioning applied to the tethers by manipulating the primary tether, or individual tether ends located on an exterior of a patient to help position and flatten the repair prosthetic. However, it should be understood that a primary tether that is separate from the individual tethers attached to the patch body may also be used as the disclosure is not so limited.

In some embodiments, it may be desirable to increase an area over which a force is applied to a repair prosthetic to mitigate curling. In one such embodiment, a repair prosthetic may include a plurality of extensions, i.e. tethers that extend out from the individual tethers used to apply forces to a patch body of the repair prosthetic to mitigate curling. These extensions may be attached to the patch body between a frame of the repair prosthetic and a periphery of the patch body at different positions along a periphery of the patch body. When forces are applied to the individual tethers, the associated extensions will apply a force to the patch body at each location the extensions are attached to. Thus, the extensions will apply the desired force to a larger portion of the patch body which may permit the use of fewer tethers to provide a desired amount of curl mitigation for a repair prosthetic.

The inventors have also contemplated that it may be desirable in some applications to have a frame that is removable from a patch body of a repair prosthetic. For example, in some embodiments, a suture may be used to connect a frame and patch body. The suture may be cut at one or more locations so the frame may be pulled away from the patch body. Alternatively, the suture may be sufficiently weak or may be modified to include one or more localized weak points that will fail upon application of a sufficient pulling force. In a separate embodiment, the frame may be adhered to a patch body by a relatively weak adhesive such that the frame may be delaminated from the patch body with a peeling force after the patch body is attached to tissue. In another embodiment, the frame and/or patch body may releasably engage each other. In one such arrangement, the patch body may include one or more slits that releasably receive a corresponding portion of the frame, such as projections, received in the slits that may be pulled out from the slits when a sufficient force is applied to the frame. In yet another embodiment, flexible coil fasteners may be used to attach the frame to the patch body such that when a sufficient force is applied, the flexible fasteners deform and disengage with the patch body to release the frame. Of course, while several attachment methods are listed, other removable attachment methods are also contemplated.

In some applications it may also be desirable to include removable tethers in a repair prosthetic. In such an embodiment, the tethers may be attached to a patch body of the repair prosthetic in manners similar to those noted above for a removable frame including, but not limited to, adhesives, sutures, weakened sutures that break under tension, deformable fasteners, and other appropriate types of attachment. For example, a non-absorbable tether could be removed from a subject's body after affixing the patch body by either severing the attachment points using surgical cutters, pulling on the tethers to break a weakened suture, and/or pulling the tethers to pull out one or more associated removable fasteners. In a specific embodiment, tethers may be tied, or otherwise affixed, to the flexible coil fasteners that are in turn inserted into the patch body. These flexible coil fasteners may have an extended, linear configuration when they are tensioned that facilitates releasing them from the patch body. The flexible coil fasteners may also have a retracted, coiled configuration when they are not tensioned to retain the tethers on the patch body. Thus, the tethers may be selectively removed after appropriately positioning and attaching a repair prosthetic to tissue.

While removable frames and/or tethers are described above, embodiments in which the frame and/or tethers of a particular repair prosthetic are absorbable are also contemplated. In such an embodiment, the frame and/or tethers of a repair prosthetic may be left in a subject where they will be absorbed over time.

In some embodiments, a frame may be in the form of a thin, flat textile structure having a bottom surface and a top surface, and at least one of the top and bottom surfaces may have a substantially flat shape. In one embodiment, the bottom surface of the frame faces the patch body and may have a flat shape and the top surface may have a curved profile. In other embodiments, a wall may be located between the long edges of the top and bottom surfaces of the frame. The frame may also be solid. The frame may be formed from any appropriate material including, but not limited to nylon material, other synthetic polymers, as well as natural materials. The frame may also be flexible to facilitate collapsing to a desired size and shape when the assembled patch body and frame are rolled up or otherwise reduced in size for minimally invasive delivery.

The various tethers described herein may be made from any biocompatible absorbable or non-absorbable elongated material including, for example, suture, fabric, mesh, polymer film, wires, cables, combinations of the forgoing, and/or any other appropriate elongated planar or filament type material. Possible non-absorbable materials include but are not limited to: polypropylene, nylon, polyester, polyvinyldene fluoride (PVDF), silk, or metal wires such as stainless steel or titanium alloys. Absorbable materials include but are not limited to various polyglycols, catgut, polyglactins, and Vicryl.

In some of the embodiments described herein, the use of a primary tether and individual tethers attached to a patch body of a repair prosthetic are described. However, it should be understood that these primary and individual tethers may be provided in any number of ways. For example, in one embodiment, a primary tether is a single tether that is connected to the separate individual tethers attached to the patch body either directly, or indirectly using an intermediate component or material. Alternatively, in another embodiment, a primary tether may be integrally formed with the individual tethers. In one such embodiment, an end of a primary tether may split to form individual tethers that extend out from the primary tether to their attachment points with the patch body. In yet another embodiment, the free ends of the individual tethers may be braided, tied, or otherwise gathered together to form a primary tether with the individual tethers extending out from that primary tether.

In view of the above, it should be understood that the various arrangements of tethers, primary tethers, and other similar structures may either be separate connected components or they may be integrally formed as the disclosure is not so limited.

It is contemplated that some embodiments may utilize tethers coated or treated with compounds to increase their biocompatibility or impart additional functionality. For instance, tethers may be coated with an anti-adhesive material or anti-bacterial material to mitigate potential post-surgical complications.

Thicknesses and lengths of tethers used with a particular repair prosthetic may vary based on the size and type of repair prosthetic used for a particular surgical procedure. However, a range of appropriate tether thicknesses include, but are not limited to, thicknesses between or equal to 0.01 mm and 1 mm, 0.01 mm and 0.8 mm, 0.02 mm and 0.7 mm, or any other appropriate thickness.

Tethers may also be attached to a patch body using any appropriate method, including, but not limited to, knots, sutures, adhesives, welds, coil fasteners, staples, and/or any other appropriate attachment method.

For the sake of clarity, the various embodiments described herein are described in connection with a repair prosthetic for repairing a hernia, specifically a ventral hernia. However, the disclosure is not necessarily so limited, and may be employed in other patch systems for other hernias, other soft tissue or muscle wall defects, as well as may other types of surgical or medical treatments. With respect to repair of a ventral hernia, the tether system and patch body may be placed in the intraperitoneal, preperitoneal, retromuscular, or other anatomical space, as the disclosure is not so limited. For case of understanding, the prosthetic is described in connection with a laparoscopic procedure for applying the prosthetic, but the disclosed devices may be employed in other minimally invasive procedures, in an open procedure, or in other techniques for repairing a hernia or other soft tissue defect as the disclosure is not so limited.

In the various embodiments described herein, a repair prosthetic may include a patch body having a first side that is intended to be positioned against a tissue or muscle wall, such as the abdominal wall, that includes a defect. The first side of the patch body may be configured for tissue ingrowth. In some applications, the opposing side of the patch may be located adjacent organs, such as the intestines or other viscera, and, thus, may include a barrier, such as a layer of barrier material or a barrier coating, to prevent adhesions between that side of the patch and the organs.

A patch body may be formed of a porous material, such as a knit fabric, woven or non-woven fabric, or may be composed of a solid, substantially non-porous, or microporous material. The patch body may be formed of one or more layers of the same or dissimilar material, and the layers may be stacked one on top of the other, side-to-side, or include a combination of both stacking arrangements. The patch body may be formed with portions that are tissue infiltratable and other portions that are less tissue infiltratable or are non-tissue infiltratable, providing selected areas of the repair device with different tissue ingrowth and adhesion resistant properties. The patch body may be formed of a permanent material, a resorbable material, or a combination of permanent and resorbable materials. It should be appreciated that the patch body may be formed of any biologically compatible material, synthetic or natural, suitable for repairing a tissue or muscle wall defect as would be apparent to one of skill in the art.

Depending on the embodiment, a patch body may include only a tissue infiltratable layer, only a solid or non-tissue infiltratable layer, or a combination of tissue infiltratable and non-tissue infiltratable aspects situated in the same layer. Additionally, various components may be described as being positioned on one side or the other of the patch body. However, the disclosed embodiments are not limited to being on any particular side of the patch body. Accordingly, it should be understood that the various components described herein may be located on either side of the patch body as the disclosure is not so limited.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

Various techniques may be employed to reduce a repair prosthetic to a smaller configuration suitable for delivery through a narrow opening, such as via a laparoscopic cannula. In one embodiment shown in FIGS. 1A and 1B, an introducer 10 may include a patch receiving area defined by two prongs 12 that a portion of the patch body is positioned between. The patch body is then rolled about the prongs of the introducer to place the repair prosthetic in a reduced configuration as shown in FIG. 1B. The repair prosthetic may then be inserted into a cannula of a medical device for delivery.

After a repair prosthetic has been inserted into the body through a cannula and expanded within the body cavity, the material forming the repair prosthetic, i.e. the frame and/or patch body, the repair prosthetic may have a tendency to at least partially curl in the direction it was rolled up in, or form a permanent crease or curl from the rolling tool that folds the mesh toward the anterior surface of the patch. FIG. 2 shows an exaggerated example of a patch body 22 of a repair prosthetic exhibiting curling and creasing. Crease 23 arises where the prongs 12 of introducer 10 gripped the patch body to begin rolling up the patch body for delivery. Separately, as a result of the rolling, an edge of the patch body rolls upwards to form curl 21. As noted previously, the presence of this curl may make it difficult to affix patch body 22 to an abdominal wall or other tissue. In embodiments where the patch body 22 was collapsed or otherwise reduced in size for delivery into the body, the patch body could also display creases or other topological defects.

Figure 3B:
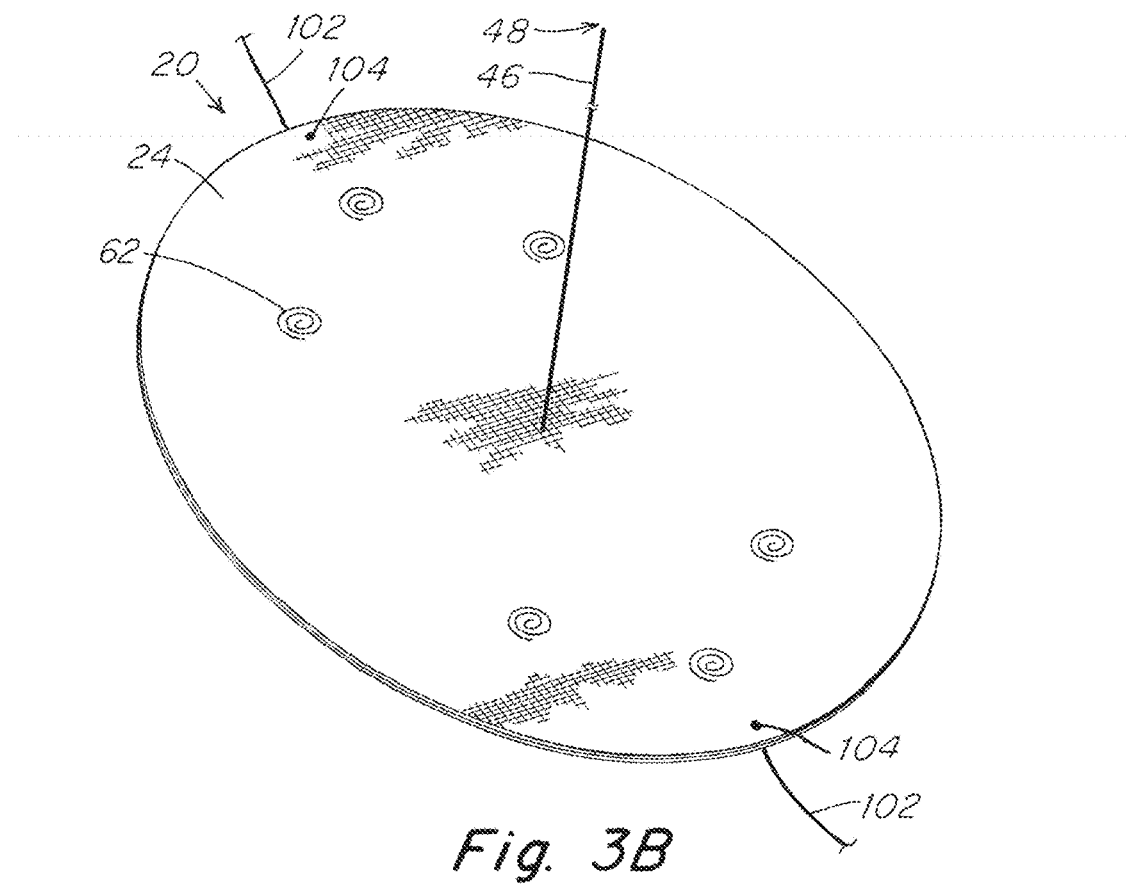
FIG. 3B shows a bottom perspective view of the repair prosthetic including a curl mitigation system of FIG. 3A.

FIGS. 3A and 3B show one embodiment of a repair prosthetic 20 for repairing a hernia or other soft tissue defect in detail. Repair prosthetic 20 may include a patch body 22 having a first surface or tissue infiltratable side 24 that is arranged for tissue ingrowth, and a second opposing surface or non-tissue infiltratable side 26. A frame 34 may be disposed on the second surface 26 of the patch body 22. Additionally, two or more tethers 102 are attached to the patch body 22 at attachment points 104 that are located between the frame and an outer periphery of the patch body. The two or more tethers are attached to two opposing portions of the patch body, and in some embodiments may be located on diametrically opposing sides of a central axis of the patch body. While two tethers have been shown, in some embodiments, a plurality of tethers may be attached to the patch body between the frame and periphery of the patch body at different positions extending around the periphery of the patch body. As detailed further below, these tethers may be tensioned to position and/or mitigate curling of the patch body during a surgical procedure.

As noted above, a frame 34 may be disposed on the second surface 26 of the patch body 22. The frame may also be spaced inward from and extend generally around a periphery of the patch body, as illustrated in FIGS. 3A and 3B. For example, the frame 34 may include an outer frame component 38 which defines a generally open interior space 40 through which fixation elements such as sutures, tacks, staples or other devices may be applied to secure the patch body to the abdominal wall. The frame may also include a cross bar 42 extending across the open frame interior and is connected to opposing portions of the outer frame component. In addition, or alternatively, the cross bar 42 may be connected to portions 44 of the frame where fasteners 62 attach the frame to the patch body and/or to other portions of the frame. The frame may have a thin or reduced profile. For example, and without limitation, the frame may be in the form of a flat sleeve or sheet so as to minimize the overall thickness of the repair prosthetic when assembled with the frame in a reduced configuration for delivery through an opening, such as a narrow incision or cannula, to the treatment site. The frame may be a continuous component or may include two or more separate portions that may either be contiguous and/or spaced from each other.

In some embodiments, a primary tether 46 may be attached to and extend from a central region of a frame 34. A free end 48 of the primary tether may pass through a thickness of the patch body 22 so that it extends beyond the side of the patch body opposite the frame through an aperture 49 formed in the frame and/or patch body. In some instances the aperture may be a central aperture formed through the frame. During a surgical procedure, the primary tether may be drawn through the abdominal wall, or other tissue, to outside of the patient using a suture passer or other device. A pulling force on the free end of the primary tether in an outward direction away from the frame and the patch body may facilitate biasing the frame and associated patch body towards, and maintaining the patch body in contact against, the abdominal wall or other tissue.

In the above embodiment, after the repair prosthetic 20 has been delivered to a surgical site, the frame 34 expands the repair prosthetic from a reduced configuration to an expanded configuration. A user may then draw the primary tether 46 to an exterior of the patient using a suture passer or other applicable tool. Once outside of the body cavity, the primary tether may be pulled to bring the frame 34 and patch body 22 into contact with the abdominal wall or other tissue. A user may then tension one, two, or any number of the tethers 102 using a grasper or other appropriate gripping instrument as needed, to position and/or tension patch body 22 to mitigate any curling or creasing of the repair prosthetic before affixing the patch body to the abdominal wall or other tissue. In instances where a single tether is tensioned, the primary tether 46 may help to maintain the patch body in a desired position. Accordingly, tensioning even a single tether 102 may apply a tension to the patch body to help mitigate curling of the repair prosthetic. With the patch body positioned flat against the abdominal wall, or other tissue, surgical fasteners, such as a sutures, tacks, staples, or any other appropriate component capable of fixating the repair prosthetic to tissue may be applied around a periphery of the patch body and/or within an interior portion of the patch body within the openings of the frame. With the patch body 22 of a repair prosthetic securely fixated to the tissue, the frame 34 and tethers 102 may optionally be detached from the anchored patch body and removed from the body cavity as detailed further below.

The depicted embodiment shows the tethers 102 knotted at diametrically opposed portions of the patch body between the frame and the periphery of the patch body. It should be understood however that the tethers may be attached in a variety of ways at a variety of locations. For instance, in some embodiments the tethers 102 are instead tied to the frame 34, or fastened to the frame using an appropriate fastener. In embodiments where the tether is attached to the frame, the tethers may be stitched to the patch body such that the tether weaves in and out of the patch body as the tether extends radially outward from the frame to the edge of the patch body where the end of the tether may freely hang from the edge of the patch body for case of manipulation. In these embodiments, tensioning the tether tensions the patch body between the edge and where the tether is tied to the frame.

In still another embodiment, tethers 102 may be stitched onto the patch body at a location at or between a frame and a periphery of the patch body. The stitched portion of the tether may extend in a radially outwards direction, and may extend beyond the periphery of the patch body as previously described. In some embodiment, the stitched portion of the tether may be attached to the frame of the repair prosthetic and the sewn portion of the tether may extend radially outward from the frame. Alternatively, in another embodiment, the stitched portion of the tether may extend across the patch body from a first portion of the patch body to a second radially opposing portion of the patch body with free ends of the tether extending out from either end of the stitching to form two tethers located on opposing sides of the patch body. Depending on the embodiment, the stitched portion of the tether may extend completely, or only partly, between two opposing edges of the patch body. In embodiments where a tether extends across an interior portion of a patch body, the tether may not be attached to the frame.

Figure 4:
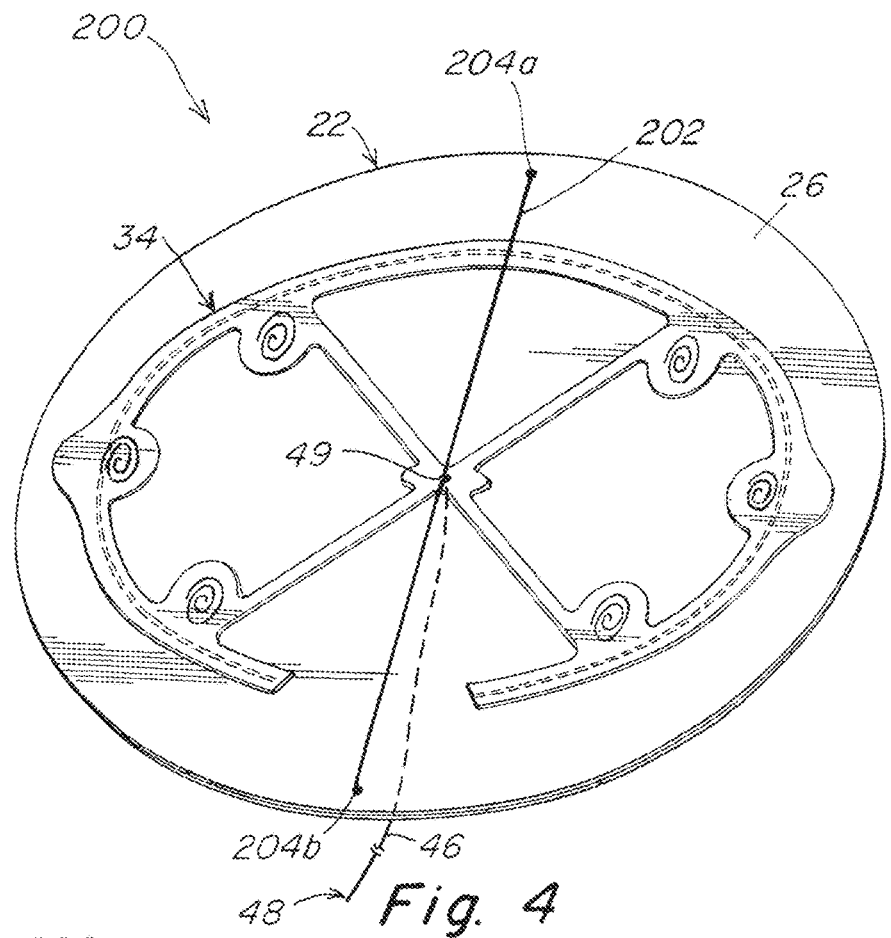
FIG. 4 shows a top right perspective view of an embodiment of a repair prosthetic including a curl mitigation system.

FIG. 4 shows another embodiment of a repair prosthetic 200. In this embodiment, two or more tethers 202 are attached to opposing portions of a patch body 22 at locations 204a and 204b between a frame 34 disposed on the patch body and an outer periphery of the patch body. The tethers may extend inwards towards an interior portion, or center, of the patch body, where they pass through an aperture 49 formed in a portion of the frame such that they extend away from the patch body and frame. Alternatively, the individual tethers may be attached to a primary tether 46 that passes through the aperture, and/or the primary tether may be formed by the individual tethers. Depending on the embodiment, the tethers and/or primary tether may pass through the patch body and/or frame from a second non-tissue infiltratable side 26 to a first tissue infiltratable surface 24 of the patch body. Alternatively, the tethers and/or primary tether extend away from the second non-tissue infiltratable surface 26 of the repair prosthetic. In either case, the individual tethers and/or primary tether may be tensioned to apply tension to the portions of the tethers attached to the patch body to apply a force to the patch body and mitigate curling present in the repair prosthetic. In embodiments where the primary tether and/or individual tethers extend out from a tissue infiltratable side of the patch body, the primary tether and/or individual tethers may be passed to an outside of the surgical cavity using a suture passer to both bias the repair prosthetic against an abdominal wall, or other tissue, as well as to apply tension to the tethers to uncurl the repair prosthetic.

In the embodiment depicted in FIG. 4, only a single pair of tethers 202 extend to opposing portions, and in some embodiments opposing diametrically opposing portions, of a patch body. However, in other embodiments, there may be multiple pairs of tethers extending between the same opposing point and the aperture in the frame. For example, tethers in the form of elongated loops may extend between the aperture and the attachment points with the patch body. In still other embodiments, a plurality of tethers may be spaced around a periphery of the patch body to permit forces to be applied to the patch body in any number of places to help mitigate curling.

In practice, after prosthetic 200 is delivered into a patient, a user may draw the primary tether 46 and/or the ends of the individual tethers to an exterior of the patient using a suture passer or other applicable tool. Once outside of the body cavity, the primary tether 46 and/or individual ends of the tethers 202 may be pulled to bring the frame 34 and patch body 22 into contact with the abdominal wall or other tissue. Once there, the user may either pull the primary tether and/or the ends of the individual tethers 202 to tension the appropriate tethers to uncurl or uncrease a desired portion of the patch body. With the patch body positioned flat against the abdominal wall, the repair prosthetic 200 may then be fixated to the tissue.

Figure 5:
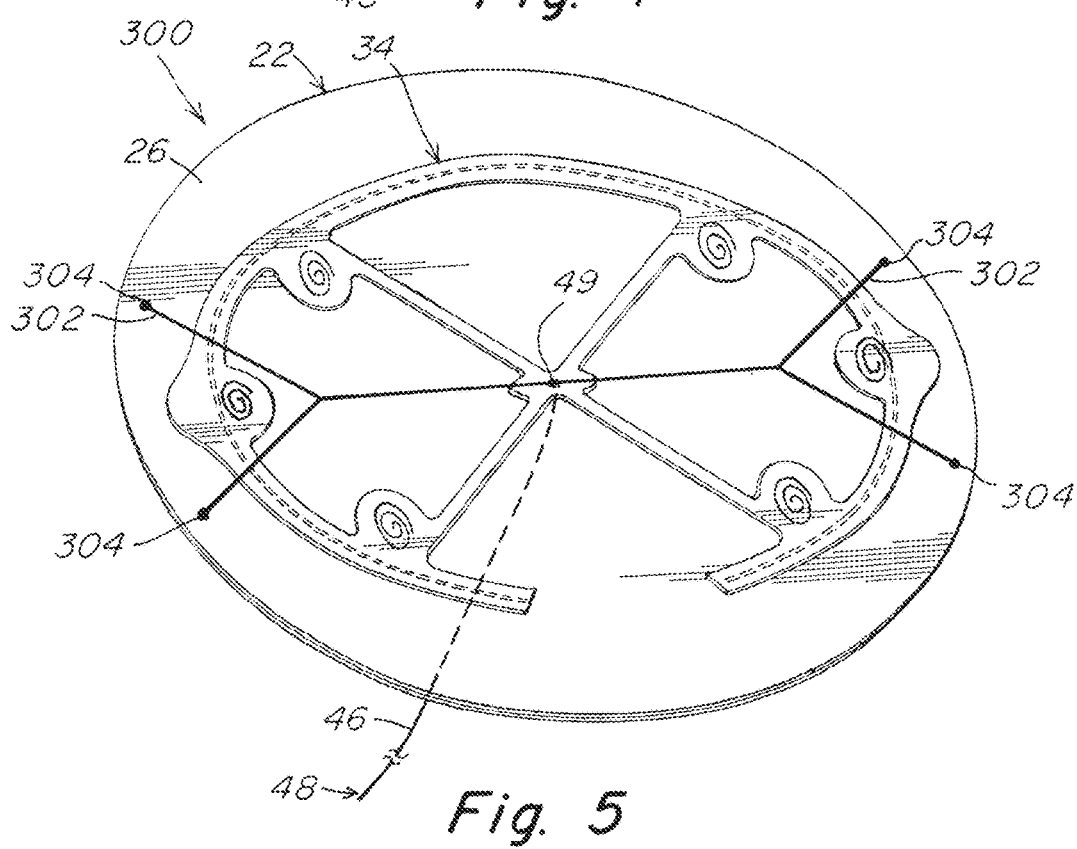
FIG. 5 shows a top left perspective view of another embodiment of repair prosthetic including a curl mitigation system.

FIG. 5 shows another embodiment of a repair prosthetic 300 that applies forces to larger sections of a patch body 22 to mitigate curling or creasing of the patch body. Similar to FIG. 4, two or more tethers 302 extend radially outwards away from a primary tether 46 and an aperture 49 formed in a frame 34. The individual tethers may include two or more extensions 302 that extend out from an end of the tether and are attached at several anchoring points 304 at locations between the frame and a periphery of the patch body. These extensions may increase an area of the patch body over which a force is applied to the patch body by the individual tethers. Accordingly when the primary tether 46, or the individual tethers are pulled, the individual tethers and associated extensions may be tensioned to apply force to the patch body at each location the extensions are attached to the patch body. While only two extensions and tethers are depicted in the figure, it should be understood that any number of tethers and any number of extensions associated with each tether may be used as the disclosure is not so limited.

Figure 6:
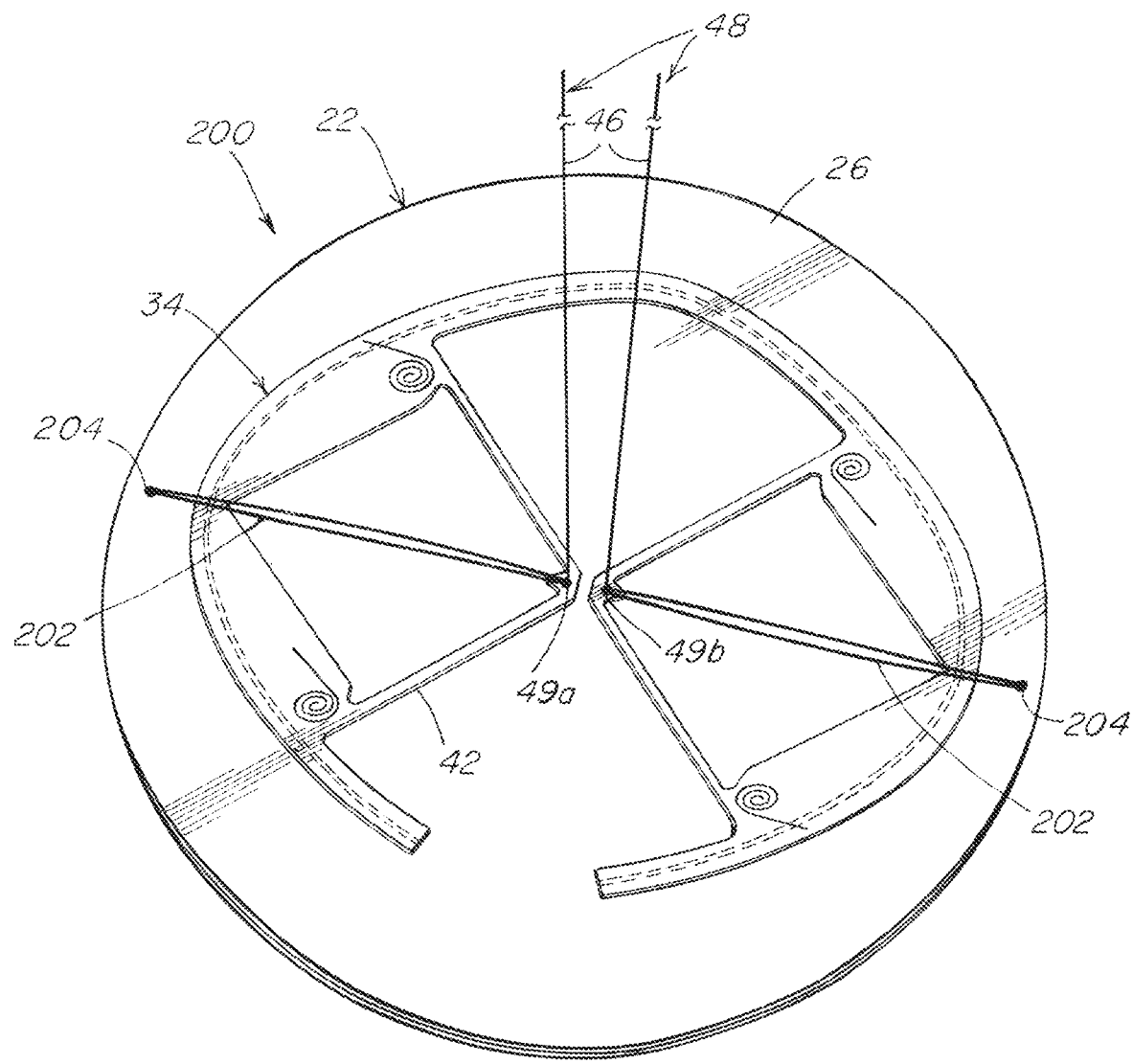
FIG. 6 shows a top right perspective view of an embodiment of a repair prosthetic including a curl mitigation system and a frame including separate moveable portions.

In some embodiments, it may be desirable to include a frame that is assembled after delivery to a surgical device to facilitate placing the repair prosthetic in a reduced configuration. FIG. 6 shows one such embodiment. Similar to the embodiment of FIG. 4, the repair prosthetic 200 includes a frame 34 and patch body 22. However, in the depicted embodiment, the frame 34 includes two or more cross bars 42 that are disconnected from one another. During use, these disconnected cross bars are connected to one another to stiffen the frame and help aid in expanding the repair prosthetic to an expanded configuration. To facilitate bringing the different cross bars together, the separate cross bars may include separate apertures 49a and 49b. Either the individual tethers 202 and/or separate primary tethers 46 may pass through these separate apertures. Accordingly, when the primary tethers and/or individual tethers are tensioned along a given direction, as may occur when reducing curl and/or biasing the repair prosthetic against tissue with a central tether extending to an exterior of a patient, the separate portions of the frame, such as the separate cross bars, may be biased towards one another to expand the frame. This may assist in spreading the patch body from a reduced configuration to an expanded configuration while simultaneously tensioning the associated tethers to mitigate curl.

While multiple primary tethers are described above in relation to FIG. 6, in some embodiments, a single primary tether that splits near the patch body may passes through each of the apertures and be attached to the separate tethers as the disclosure is not so limited.

Figure 7A:
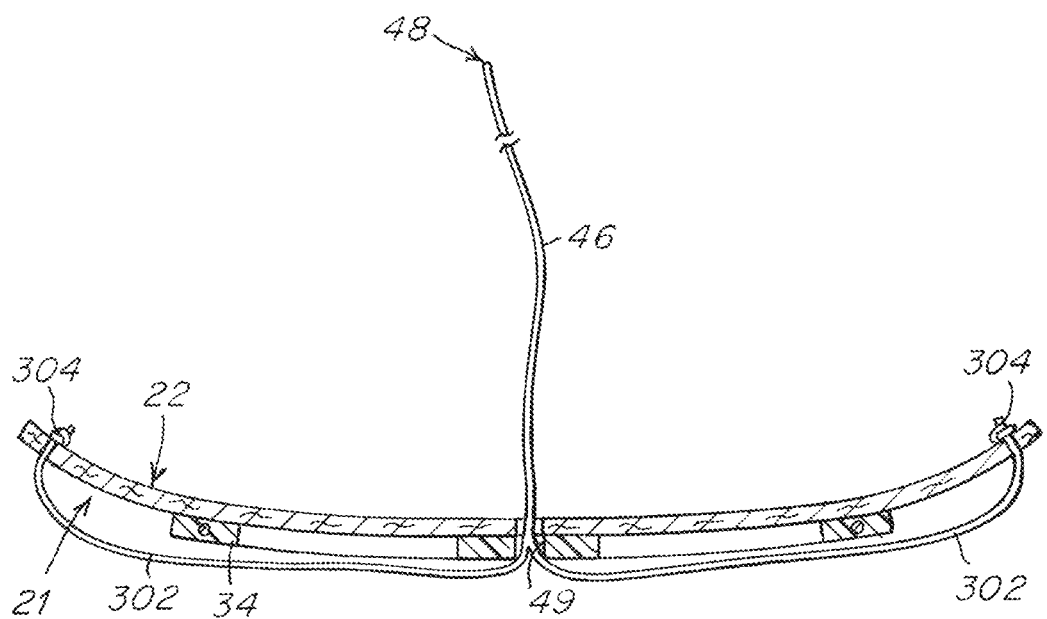
FIG. 7A shows a diagrammatic cross-sectional view of an embodiment of a repair prosthetic including a curl mitigation system before tensioning.
Figure 7B:
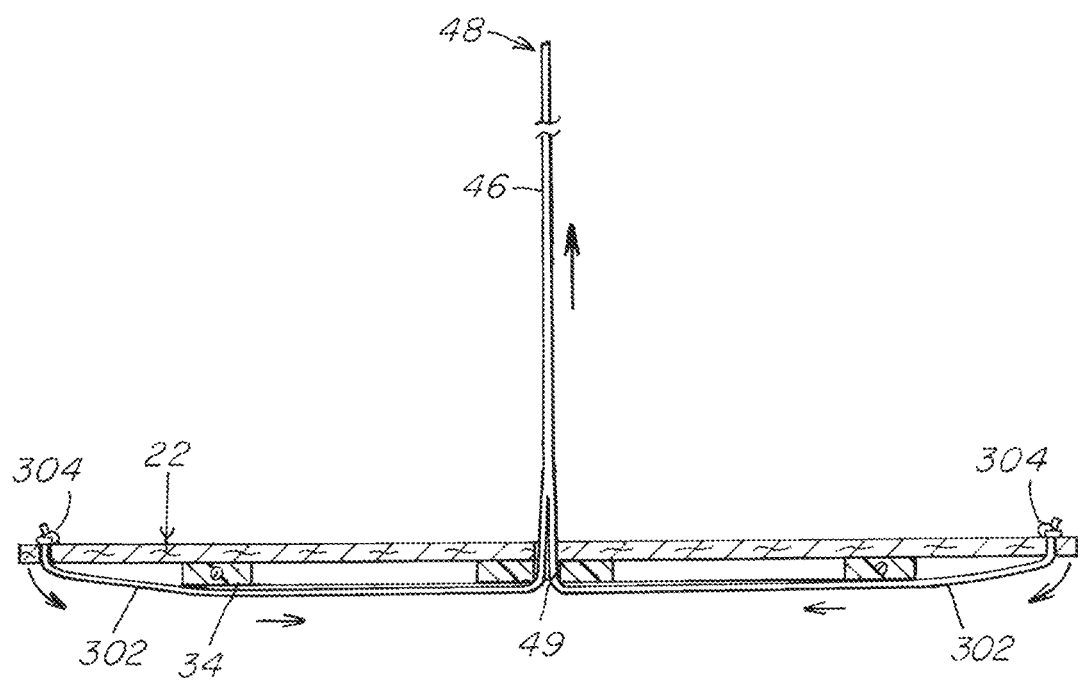
FIG. 7B shows a diagrammatic cross-sectional view of the embodiment of the repair prosthetic of FIG. 7A after tensioning.

FIGS. 7A and 7B show a cross-sectional view of a repair prosthetic during a curl mitigation procedure. FIG. 7A shows a patch body 22 prior to curl mitigation as evidenced by curl 21. As the user pulls on a free end 48 of a primary tether 46, the individual tethers 302 attached at anchor points 304 located between a periphery of the patch body and frame are also tensioned. With frame 34 maintaining a central portion of the patch body relatively flat and rigid, an anti-curling force and/or moment is applied to the patch body at anchor points 304 which pulls the edges of the patch 22 downwards to at least partially remove curl 21 as seen in FIG. 7B.

Figure 8:
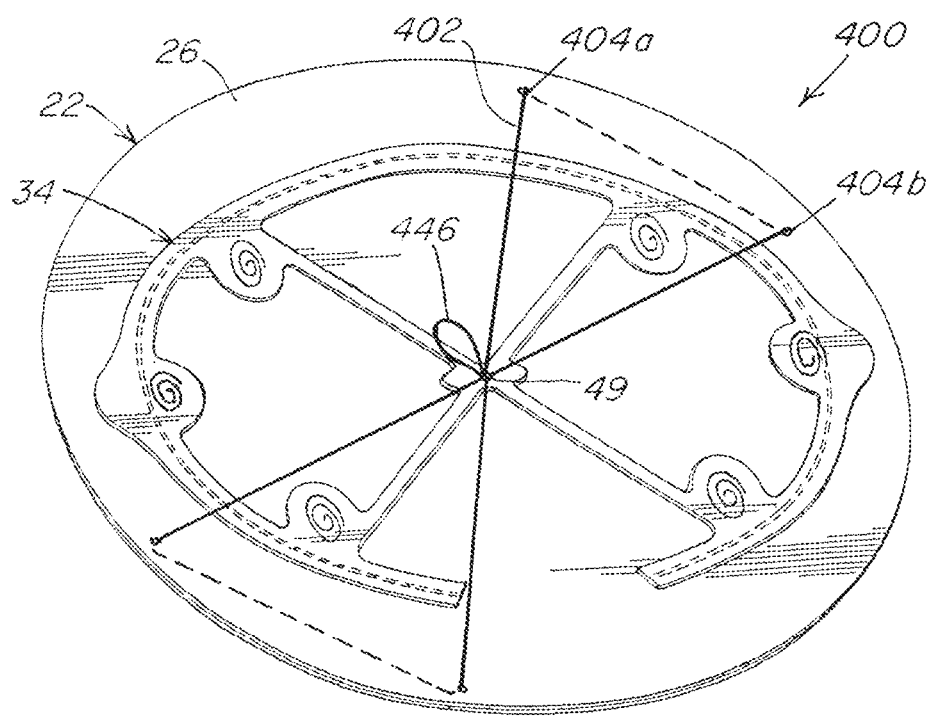
FIG. 8 shows a top left perspective view of another embodiment of a repair prosthetic including a curl mitigation system with adjustable tensioning.
Figure 9:
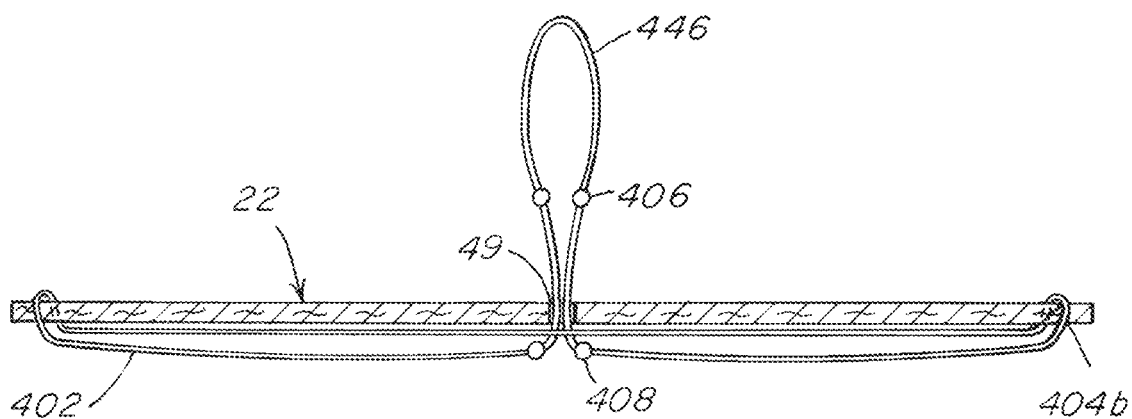
FIG. 9 shows a diagrammatic cross-sectional view of the curl mitigation system of FIG. 8.

FIGS. 8 and 9 show another embodiment of a repair prosthetic 400 including a system that may be used to adjust the tensioning of the one or more tethers used to mitigate curling of the repair prosthetic. In this embodiment a looped primary tether 446 is used in place of a single primary tether. The looped primary tether 446 may extend through an aperture 49 formed in the frame and/or patch body as previously described. Individual tethers 402 attached to the separate portions of the looped primary tether may then be attached to the patch body at a location between a periphery of the patch body and the frame. For example, in the depicted embodiment a tether 402 extends from the aperture and passes through the patch body 22 at a first location 404a prior to extending back through patch body 22 again at a second location 404b and then back to the aperture 49. The two ends of the tether extending through the aperture may then be connected to one another to form the noted loop extending out from the aperture. Similar loop arrangements may be used with other pairs of tethers as well. As detailed further below, the loop arrangement allows a user to grip the loop and pull the entire looped primary tether 446 to generally apply tension to the various individual tethers. The user may then pull the separate portions of the loop to change a tension applied to the separate tethers, thereby applying different amounts of force and/or displacement to the different sides of the patch body 22. A user may either clamp, or otherwise immobilize, the tethers to maintain a desired level of tension and/or displacement. Alternatively, the aperture and tethers may be sized and shaped, or otherwise configured, to maintain a desired displacement and/or tensioning of the tethers using for example friction.

As best shown in FIG. 9, the looped primary tether 446 may include two or more stops, such as knots or beads of material, located on either side of the aperture formed in the frame for each tether connected to the loop. The stops prevent the looped primary tether 446 from slipping through the aperture 49. The stops may also be positioned at a location along the individual tethers such that they prevent a user from applying excessive tensioning and/or displacement of the tethers to help prevent creating an opposing curl of the patch body periphery.

In practice, after a prosthetic 400 is delivered into a patient, a user may pull on the looped primary tether 446 which will generally tension the individual tethers 402. This action applies an uncurling force to corresponding sides of the patch 22. The user may then pull on different sides of the loop associated with different tethers to adjust an amount of tension and/or displacement applied to the individual tethers. As noted above, the stops 406 and 408 may prevent the looped primary tether from slipping through the repair prosthetic and/or applying a reverse curl to the patch body. Once the patch body is flattened to the user's satisfaction, the patch body may then be fixated to the abdominal wall or other tissue.

It should be understood that while an embodiment including a looped primary tether has been described, embodiments in which a separate primary tether and a loop for tensioning the individual tethers are used are also contemplated as the disclosure is not so limited. For example, a primary tether could still be used to bring the repair prosthetic into contact with tissue and a separate tether system and loop arrangement may permit a user to adjust tensioning of the tethers. Additionally, while stops associated with a looped primary tether have been described, it should be understood that stops may be associated with each individual tether such that the stops are located on either side of an aperture the tether passes through. Therefore, a tension and/or displacement may be individually adjusted for each tether.

Figure 10:
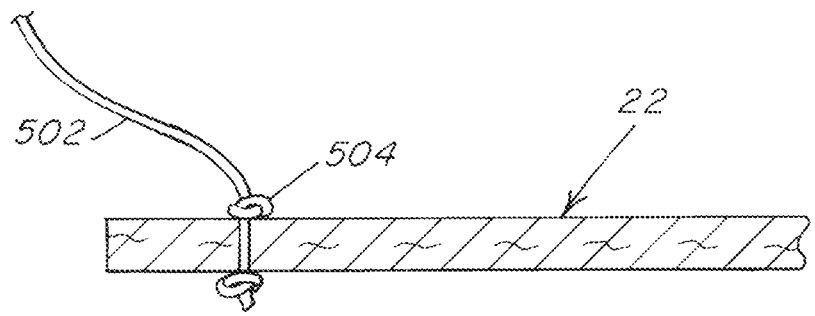
FIG. 10 is a schematic cross sectional view of a tether attached to a repair prosthetic with a knot.

It should be understood that the various tethers described herein may be attached to a patch body in any number of ways. For example, FIG. 10 shows one embodiment for anchoring tethers to a patch body 22. In this arrangement, tethers 502 pass through patch body 22 at anchor point 504. The tether 502 is then knotted on both the first side 24 and second side 26 of the patch body 22 to prevent slipping out of either side. Alternatively, beads of material attached to the tether may be used on either side of the patch body. Additionally, other types of attachment methods that may be used include, but are not limited to, sutures, adhesives, welds, mechanical fasteners such as coils fasteners and staples, and/or any other appropriate method for attaching the tethers to the patch body 22 as the disclosure is not so limited.

Figure 11:
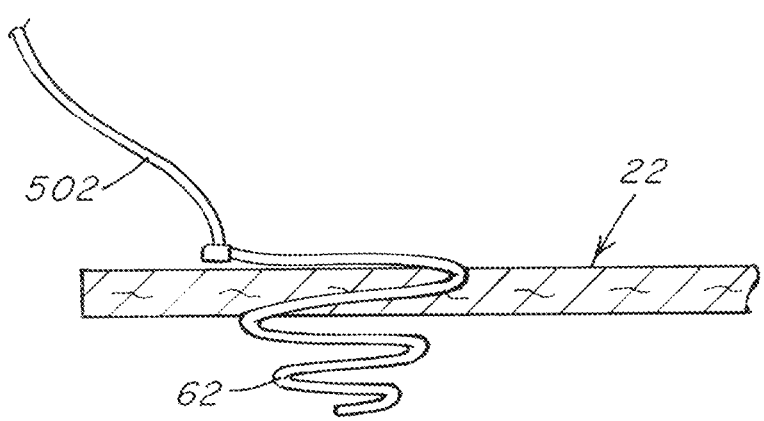
FIG. 11 is a schematic cross sectional view of a tether attached to a repair prosthetic with an elastic releasable coil fastener.

As seen in FIG. 11, a tether 502 may be releasably attached to a patch body 22 via one or more flexible coil fasteners 62. In one embodiment, the coil fastener has a relaxed configuration, such as a substantially coiled configuration as shown in the figure, to retain the tether on the patch body. The coil fastener may also have a loaded configuration, where the coil fastener may become elongated and/or substantially straight when tensioned. When loaded in this manner, the coil fastener may detach from the patch body. Thus, the flexible coil fastener permits the selective connection and release of the tether with the patch body. In some instances, the flexible coil fastener may attach both the tether and a frame of the repair prosthetic to the patch body. For example, FIG. 3A shows a frame 38 connected to a patch body 22 by coil fasteners 62 which may be located anywhere along the frame including at portions 64 of the frame. Thus, a user may use a grasper or other laparoscopic instrument to grip and pull the frame and/or tether away from the patch with a force beyond what is necessary to mitigate curling. In response to the pulling force, the coil fasteners extend to the loaded or straight configuration (i.e., linear or substantially linear) allowing the coil fasteners to slide out of the fixated patch body releasing the frame and/or tethers depending on the particular embodiment. The now unattached tethers and/or frame may then be easily removed from the surgical cavity through a minimally invasive opening, such as a laparoscopic cannula, trocar, or narrow incision via which the assembled frame and patch were originally delivered to the surgical site.

Figure 12:
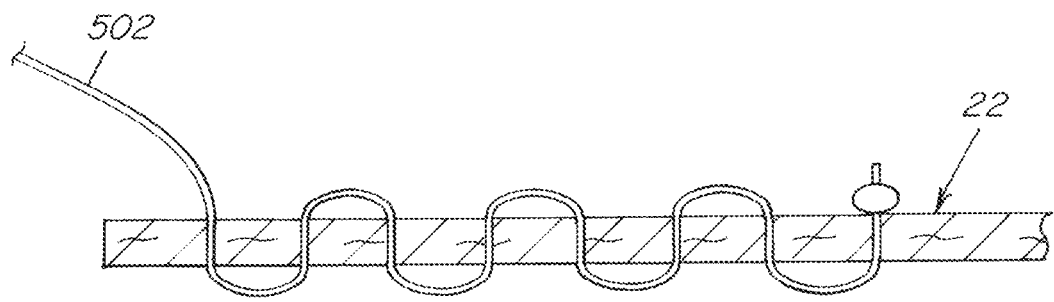
FIG. 12 is a schematic cross sectional view of a tether attached to a repair prosthetic with a sewn connection.

FIG. 12 shows another embodiment for anchoring tethers to a patch body 22. In the depicted embodiment, a tether 502 is sewn onto the patch body 22 such that the tether passes in and out of the patch body to form a sewn length of tether attached to the patch body. Similar to the above, an end of the suture may include a knot to anchor an end of the tether to the patch body. Alternatively, different types of attachment methods may be used, or the tether may be sewn onto the patch body using a stitch that does not permit the tether to be pulled out from the patch body. In instances where a loose form of stitching is used, the tether may be pulled out from the patch body to permit selective removal of the tethers after a repair prosthetic has been deployed.

The foregoing description of various embodiments are intended merely to be illustrative thereof and that other embodiments, modifications, and equivalents are within the scope of the invention recited in the claims appended hereto.

The invention claimed is:

1. A prosthetic comprising:
a patch body having a periphery;
a frame attached to the patch body, wherein the frame assists in spreading the patch body from a reduced configuration to an expanded configuration, and wherein the frame includes one or more apertures; and
one or more tethers, wherein each of the one or more tethers is attached to the patch body at an attachment location with the patch body located radially outward from the frame, wherein each of the one or more tethers includes a free end, and wherein pulling on the free end of each of the one or more tethers applies tension to the one or more tethers to spread the patch body.

2. The prosthetic of claim 1, wherein the one or more tethers is a plurality of tethers, and wherein the free end of each of the one or more tethers is gathered together to form a primary tether.

3. The prosthetic of claim 1, wherein the free end of each of the one or more tethers passes through a thickness of the patch body such that the free end of each of the one or more tethers extends beyond a side of the patch body opposite the frame.

4. The prosthetic of claim 3, where the free end of each of the one or more tethers extends through the one or more apertures of the frame.

5. The prosthetic of claim 1, wherein pulling on the free end of each of the one or more tethers is configured to bias the frame and the patch body into contact against a hernia defect.

6. The prosthetic of claim 1, wherein the one or more tethers includes two tethers, and wherein the two tethers are located on radially opposing sides of the patch body.

7. The prosthetic of claim 1, wherein the one or more tethers are releasably attached to the patch body.

8. The prosthetic of claim 1, wherein each tether of the one or more tethers includes a plurality of extensions attached to the patch body, wherein the plurality of extensions extend in different directions radially outwards from the associated tether of the one or more tethers.

9. The prosthetic of claim 1, wherein the one or more tethers comprise materials selected from the group consisting of suture, fabric, mesh, polymer film, wire, cable, and combinations of the foregoing.

10. A method of repairing a hernia defect, the method comprising:
delivering a prosthetic for repairing a hernia defect in a reduced configuration through an opening into a patient, the prosthetic includes a patch body having a periphery;
tensioning one or more tethers which are each attached to the patch body at an attachment location between a frame attached to the patch body and the periphery of the patch body, wherein each of the one or more tethers includes a free end, and wherein pulling on the free end of each of the one or more tethers applies tension to the one or more tethers to spread the patch body; and spreading the patch body to an expanded configuration about the hernia defect with the frame and the one or more tethers.

11. The method of claim 10, wherein the one or more tethers is a plurality of tethers, and further comprising gathering the free end of each of the one or more tethers together to form a primary tether.

12. The method of claim 10, further comprising passing the free end of each of the one or more tethers through a thickness of the patch body such that the free end of each of the one or more tethers extends beyond a side of the patch body opposite the frame.

13. The method of claim 12, where the free end of each of the one or more tethers extends through one or more apertures of the frame.

14. The method of claim 10, wherein pulling on the free end of each of the one or more tethers is configured to bias the frame and the patch body into contact against the hernia defect.

15. The method of claim 10, wherein the one or more tethers includes two tethers, and wherein the two tethers are located on radially opposing sides of the patch body.

16. The method of claim 10, further comprising releasing the one or more tethers from the patch body.

17. The method of claim 10, wherein tensioning the one or more tethers further comprises tensioning a plurality of extensions extending in different directions radially outwards from the one or more tethers.

18. The method of claim 10, wherein the one or more tethers comprise materials selected from the group consisting of suture, fabric, mesh, polymer film, wire, cable, and combinations of the foregoing.

* * * * *

UNITED STATES PATENT AND TRADEMARK OFFICE
CERTIFICATE OF CORRECTION

| | | |
|---|---|---|
| PATENT NO. | : 12,295,826 B2 | Page 1 of 1 |
| APPLICATION NO. | : 18/604732 | |
| DATED | : May 13, 2025 | |
| INVENTOR(S) | : Jonathan Bruce Trexler et al. | |

It is certified that error appears in the above-identified patent and that said Letters Patent is hereby corrected as shown below:

In the Specification

At Column 7, Line 34, please delete "case" and insert -- ease --

At Column 10, Line 13, please delete "case" and insert -- ease --

Signed and Sealed this
Nineteenth Day of August, 2025

Coke Morgan Stewart
*Acting Director of the United States Patent and Trademark Office*